United States Patent [19]

Jones et al.

[11] 4,145,346

[45] Mar. 20, 1979

[54] PREPARATION OF 3β-HYDROXY-27-NORCHOLEST-5-ENE-25-ONE AND INTERMEDIATES THEREOF

[75] Inventors: Howard Jones, Holmdel; Robert A. Frankshun, Kenilworth, both of N.J.

[73] Assignee: Merck & Co., Inc., Rahway, N.J.

[21] Appl. No.: 838,601

[22] Filed: Oct. 3, 1977

[51] Int. Cl.$^2$ ............................................. C07J 9/00
[52] U.S. Cl. ......................... 260/239.55 C; 260/397.1; 260/397.2
[58] Field of Search ................ 260/239.55, 239.55 C, 260/397.2

[56] References Cited

U.S. PATENT DOCUMENTS

| 3,786,062 | 1/1974 | Schroeder et al. | 260/397.2 |
| 3,936,478 | 2/1976 | Takeshita et al. | 260/397.2 |
| 4,028,349 | 6/1977 | Partridg, Jr. et al. | 260/397.2 |
| 4,069,321 | 1/1978 | Jones et al. | 260/397.2 |

*Primary Examiner*—Ethel G. Love
*Attorney, Agent, or Firm*—Mario A. Monaco; Martin L. Katz; Edmunde D. Riedl

[57] ABSTRACT

A process for preparing 3β-hydroxy-27-norcholest-5-ene-25-one, a useful intermediate in the synthesis of 25-acetoxy vitamin D$_3$, novel intermediates, and preparation thereof are disclosed.

5 Claims, No Drawings

PREPARATION OF 3β-HYDROXY-27-NORCHOLEST-5-ENE-25-ONE AND INTERMEDIATES THEREOF

DISCLOSURE OF THE INVENTION

This invention relates to a new and useful process for preparing 3β-hydroxy-27-norcholest-5-ene-25-one, as well as to novel intermediates obtained therein; and to the process for preparing such intermediates. The 3β-hydroxy-27-norcholest-5-ene-25-one prepared by the novel process of the instant invention is readily converted by techniques already well known in the art into 25-hydroxy- vitamin $D_3$ which is a useful therapeutic agent in antirachitic applications (see Halkes et al, Investigations on Sterols., XXXV-Synthesis of 25-Hydroxycholecalciferol, Rec. Trav. Chim. Pays-Bas (RECUEIL), 88, 1,080–1,083, (1969)).

In accordance with the invention, 3β-hydroxy-27-norcholest-5-ene-25-one has the following structural formula:

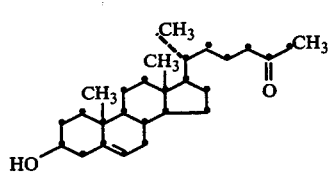

VIII

The overall process according to the invention is illustrated by the following flow sheet and in the accompanying description of the individual steps therein. The starting material, stigmasterol, or more strictly 3β-hydroxy-24-ethyl-Δ$^{5,22}$-cholestadiene, is a known compound, either available commercially or readily prepared by processes already fully described in the literature.

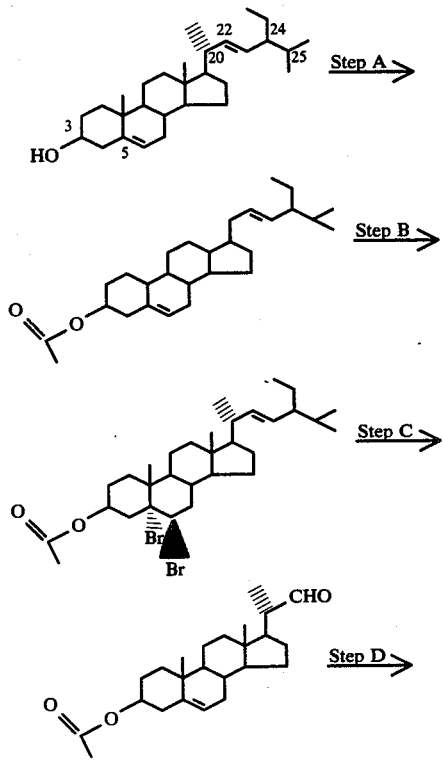

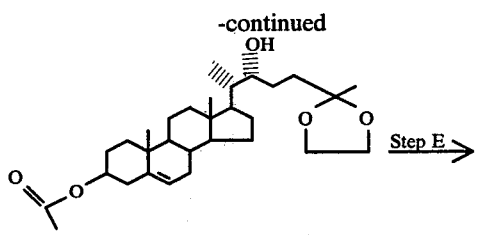

V

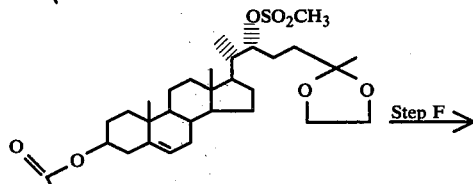

VI

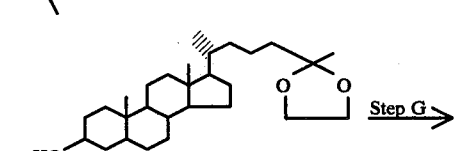

VII

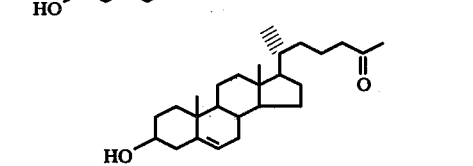

VIII

STEP A

Acylation of 3β-Hydroxy-24-ethyl-Δ$^{5,22}$-cholestadiene (Stigmasterol)

The acylation of stigmasterol is necessary so as to block the 3-position from reaction in subsequent steps. The preferred blocking group is an acyl group and the reaction can be readily performed by the reaction of the stigmasterol with at least an equimolar quantity of base and a suitable acid anhydride. The preferred anhydride is acetic anhydride. The reaction does not require additional solvent, although convenience may indicate the use of an inert solvent such as diethyl ether, tetrahydrofuran, benzene, etc. After completion of the addition of anhydride, the reaction mixture is heated at reflux for about 1 to 3 hours or until reaction is substantially complete. The reaction mixture is then cooled, filtered and most suitably further purified by recrystallization from lower alkanols.

STEP B

Halogenation of 3β-Acetoxy-24-Ethyl-Δ$^{5,22}$-cholestadiene

In order to protect the 5-position unsaturation from oxidation during the subsequent step, it is required to dihalogenate this double bond. The reaction is most preferably conducted with bromine, although chlorine would suffice. The reaction proceeds by admixing the cholestadiene acetate with at least a mole of halogen and a suitable solvent such as chloroform, carbon disulfide, carbon tetrachloride, ether tetrahydrofuran. The reaction is substantially spontaneous at 20° C., but it is preferable to hold the reaction mixture at ambient temperatures for 1 to 2 hours to insure a most complete reaction. Because the halogenation produces a number of isomers there is little point in attempting additional purification, or any need to separate the isomers.

STEP C

Ozonization and Reduction of the 3β-Acetoxy-5α,6β-dihalo-24-ethylcholest-22-ene The ozonization is readily carried out by treating with ozone the 3β-acetoxy-5α,6β-dihalo-24-ethylcholest-22-ene, the compound of formula III in a suitable organic solvent, such as methylene chloride or a mixture of methylene chloride and pyridine or methanol, at low temperature, about −70° C. to −80° C. until the required amount of ozone is taken up. The reaction mixture is allowed to warm to room temperature and the ozonide is then reduced in situ with zinc dust and acetic acid to produce the desired hexanoraldehyde, the compound of formula IV. The recovered aldehyde may be purified by chromatography over silica gel eluting with ethyl acetate in benzene.

STEP D

Alkylation of 3β-Acetoxy-cholest-5-ene-20β-carboxaldehyde

The alkylation is carried by treating 3β-acetoxy-cholest-5-ene-20β-carboxaldehyde, the compound of formula IV with the Grignard reagent, 2-(1,3-dioxolane-2-methyl)-ethylmagnesium bromide, prepared in situ by adding 2-(1,3-dioxolane-2-methyl)ethyl bromide (Bul. Soc. Chem. France, II, 2575, (1963)) in tetrahydrofuran to a mixture of magnesium and iodine in tetrahydrofuran. The hexanoraldehyde in tetrahydrofuran solution is added to the preformed Grignard reagent in the cold, about −20° C. to −40° C., and the mixture is stirred for 20 to 60 minutes. The reaction is quenched with saturated ammonium chloride and the reaction mixture is extracted with methylene chloride and water. The organic phase is separated, dried and evaporated to dryness. The residue is purified by preparative thin layer chromatography on silica gel plates eluting with ethyl acetate to obtain the ketal of formula V.

STEP E

Mesylation of the 22-Hydroxy Group

The compound prepared in Step D is dissolved in a suitable organic solvent such as pyridine and treated with methanesulfonyl chloride. The reaction conveniently is carried out at room temperature and usually requires from 12 to 24 hours for completion. The reaction mixture is quenched with ice water and the recovered precipitate is employed in the next step wihout further purification.

STEP F

Reductive Elimination of the Methanesulfonate Group

The crude mesylate prepared in Step E in a suitable solvent such as tetrahydrofuran is treated with lithium aluminum hydride in small portions at room temperature. After addition of the hydride the reaction mixture is refluxed for 18 to 36 hours, cooled to 0° C. to 10° C. and quenched with water and ethyl acetate. The reaction mixture is extracted with methylene chloride and the crude product is obtained by evaporation of the methylene chloride phase.

The ketals of formula V, VI and VII, respectively, are novel compounds and constitute the composition of matter aspect of the instant invention.

STEP G

Removal of the Ketal Group

The ketal prepared in Step F is stirred at room temperature with a mixture of acetic acid and water for 12 to 24 hours and then is extracted with methylene chloride and water. The organic phase is separated, dried, filtered and concentrated to dryness. The product may be purified by preparative thin layer chromatography on 1000 M silica gel plates eluting with 20% ethanol in ethyl acetate. The product so obtained is recrystallized from ethyl acetate to give 3β-acetoxy-27-norcholest-5-ene-25-one.

As noted above, the 3β-acetoxy-27-norcholest-5-ene-25-one prepared in accordance with the process of the instant invention is readily converted by techniques well known in the art into 25-acetoxy vitamin $D_3$. Thus, 3β-acetoxy-27-norcholest-5-ene-25-one in dry benzene may be treated with methyl magnesium bromide at about 5° C. The reaction mixture is stirred for 8 to 18 hours and then is worked up by the addition of an aqueous solution of ammonium chloride. The cholest-5-ene-3β-25-diol so produced is crystallized from successively tetrahydrofuran diisopropyl ether and tetrahydrofuran ethyl acetate.

This diol was allylically brominated with dibromodimethyl hydantoin at 60° in cyclohexane to give choles-5-en-7α-bromo-3β,25-diol.

This bromo diol was dehydrobrominated with S-collidine at 140° to give cholest-5,7-diene-3β,25-diol.

This diol is dry and peroxide free tetrahydrofuran is irradiated under nitrogen using a 450 Biosol beta lamp for 45 minutes. Addition of dry ether and concentration yields unchanged starting material. Chromatography of the residue over silica gel followed by crystallization from acetone gives 25-hydroxy vitamin $D_3$.

The following examples further illustrate the preferred embodiments of this invention.

EXAMPLE 1

3β-Hydroxy-27-norcholest-5-ene-25-one

STEP A

Acylation of Stigmasterol

There is dissolved in 150 ml. of pyridine 100 g. of stigmasterol and 100 ml. of acetic anhydride. The solution is heated at reflux for two hours, cooled and poured into 4 l. of water. The mixture is filtered, dried in air for 24 hours and then recrystallized from 2 l. of ethanol. There are obtained 107.5 g. 3β-acetoxy-24-ethyl-$\Delta^{5,22}$-cholestadiene having a melting point of 141° C. to 142° C.

STEP B

Bromination of Stimasteryl Acetate

To 50 g. (0.11 m.) of 3β-acetoxy-24-ethyl-$\Delta^{5,22}$-cholestadiene in 200 ml. of chloroform at 0° C. is added 5.7 ml. (0.11 m.) of bromine in 200 ml. of chloroform. After aging for one hour, the chloroform is removed by distillation under reduced pressure. There remains 68 g. of a green solid. This 3β-acetoxy-5α,6β-dibromo-24-ethyl-22-cholest-5-ene is employed without further purification in the next step.

STEP C

Ozonization of 3β-Acetoxy-5α,6β-dibromo-24-ethyl-22-cholest-5-ene

Dissolve 6.069 gm. of the product from Step B above, in 200 ml. of methylene chloride and 2 ml. of pyridine and ozonize on a Welsbach ozonizer at about 78° C. for 16 minutes at 0.94 mmole/min. (1.5 eq.). Reduce the ozonide in situ with 4.6 gm. of zinc dust and 20 ml. of acetic acid by stirring for 30 minutes at room temperature. Wash the reaction mixture with two 100 ml. portions of 0.1 N hydrochloric acid followed by two 100 ml. portions of saturated aqueous sodium bicarbonate solution. Separate the methylene chloride layer, dry over magnesium sulfate, filter and concentrate the filtrate to dryness in vacuo. Chromatograph the residue on 350 gm. of silica gel and elute with 20% ethyl acetate in benzene, m.p 120°–122° (dec.).

STEP D

Grignard Reaction on 3β-Acetoxy-27-hexanorcholest-5-en-20β-carboxaldehyde

Place 40 mg. of magnesium powder, 5 ml. of dry tetrahydrofuran and a crystal of iodine into a 15 ml., 3-neck round-bottom flask. Add 210 mg. of 2-(1,3-dioxolane-2-methyl)ethyl bromide dissolved in 2 ml. of dry tetrahydrofuran. Stir the mixture at 30° C. to 40° C. for one hour while adding 200 mg. of excess 2-(1,3-dioxolane-2-methyl)ethylbromide. Cool the mixture to −30° C. and add 500 mg. of the 3β-acetoxy-5α,6β-dibromo-24-ethyl-22-cholest-5-ene from Step C in 5 ml. of tetrahydrofuran. Stir the mixture for 30 minutes and add 10 ml. of saturated ammonium chloride solution. Extract the reaction mixture with 50 ml. of methylene chloride and 50 ml. of water. Separate the organic phase, dry over magnesium sulfate, filter and evaporate to dryness in vacuo. Purify by preparative thin layer chromatography on 1000μ silica gel plates eluting with ethyl acetate.

STEP E

The 22-Methanesulfonate of 25-Dioxalanyl-22-hydroxy-27-norcholest-5-en-3β-acetate Dissolve 2.72 gm. of the alcohol of Step D in 35 ml. of dry pyridine and add 6.3 ml. of methanesulfonyl chloride over a one-hour period. Continue stirring for an additional 18 hours. Pour the reaction mixture into 200 ml. of ice water slurry. Separate the precipitate by filtration and dry at 70° C. over phosphorous pentoxide.

STEP F

3β-Hydroxy-25-dioxalanyl-27-norcholest-5-ene

Dissolve 680 mg. of crude dioxalane from Step E in 35 ml. of dry tetrahydrofuran. Add 680 mg. of lithium aluminum hydride in portions with stirring at room temperature over a one-hour period. Reflux the reaction mixture for 24 hours and cool to 0° C. to 10° C. Add 1 ml. of ethyl acetate then 20 ml. of water to destroy the excess lithium aluminum hydride. Extract with 100 ml. of methylene chloride. Separate the organic phase, dry over magnesium sulfate, filter and evaporate the filtrate to dryness.

STEP G

3β-Hydroxy-27-norcholest-5-en-25-one

Dissolve 80 mg. of the 25-dioxalane of Step F in 3 ml. of acetic acid and 1 ml. of water. Stir the mixture at room temperature for 18 hours. Extract the reaction mixture with two 20 ml. portions of methylene chloride containing 5 ml. of water. Separate the organic phase, dry over magnesium sulfate, filter and concentrate the filtrate to dryness. Purify by preparative thin layer chromatography on 1000 M silica gel plates eluting with 2% ethanol in ethyl acetate. Crystallize the product from ethyl acetate (m.p. 119°–120°, lit. 118°–119°, J. Amer. Chem. Soc., 72, 4247–4248 (1950)).

EXAMPLE 2

A 350 mg. portion of 3β-hydroxy-27-norcholest-5-ene-25-one obtained by means of Step G of Example 1 is dissolved in 4 ml. of pyridine. To this solution is added 5 ml. of acetic anhydride, the reaction allowed to proceed at ambient room temperature for 1½ hours. The reaction mixture is extracted with 100 ml. of hexane, washed twice with 50 ml. portions of water, then washed three times with 100 ml. portions of 2.5 N HCl and then again washed with 100 ml. portions of water. The combined washed extract is then dried over anhydrous magnesium sulfate, concentrated under vacuum to a soft white solid yielding 270 ml. of 3β-acetoxy-27-norcholest-5-ene-25-one melting at 141° C. to 143° C. (lit., m.p. 138.5°–139.5°, J. Amer. Chem. Soc., 72, 4248–4250 (1950)).

EXAMPLE 3

The 3β-acetoxy-27-norcholest-5-ene-25-one from Example 2 is reacted according to the procedure of A. I. Ryer, W. H. Gebert and N. M. Murrill, J. Am. Chem. Soc. 72, 4247 (1950) to give cholest-5-ene-3β,25-diol.

EXAMPLE 4

The cholest-5-en-3β,25-diol from Example 3 is reacted according to the sequence described by Halkes and Van Vliet in Recueil. Chim., Pay-Bas, 88, 1080–1083 (1969) to give 25-hydroxy vitamin D₃.

3β-Acetoxy-27-norcholest-5-en-25-one (Example 2) can also be reacted as described in Halkes and Van Vliet's paper to give ultimately 25-hydroxy vitamin D₃.

What is claimed is:

1. A process for preparing 3β-hydroxy 27-norcholest-5-ene-25-one of the formula:

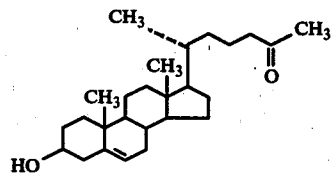

which comprises:
(a) ozonizing a 3β-loweralkanoyloxy-5α,6β-dibromo-24-ethylcholest-22-ene at −70° C. to −80° C. and reducing in situ with zinc dust and acidic acid the ozonide so formed to produce 3β-loweralkanoyloxy-27-hexanorcholest-5-en-20β-carboxaldehyde;
(b) alkylating 3β-loweralkanoyloxy-27-hexanorcholest-5-en-20β-carboxaldehyde with 2-(1,3-dioxolane-2-methyl)-ethyl bromide at −20° C. to −40° C. to produce 25-dioxalanyl-22-hydroxy-27-norcholest-5en-3β-alkanoate;

(c) treating 25-dioxalanyl-22-hydroxy-27-norcholest-5-en-3β-alkanoate with methyl sulfonyl chloride to produce 22-methane sulfonate of 25-dioxalanyl-22-hydroxy-27-norcholest-5-en-3β-alkanoate;

(d) reducing the 22-methane sulfonate with lithium aluminum hydride and refluxing said mixture followed by cooling to 0° C. to 10° C. to produce 3β-hydroxy-25-dioxalanyl-27-norcholest-5-ene; and (e) treating the 25-dioxalanyl compound with dilute acids to produce 3β-hydroxy-27-norcholest-5-en-25-one.

2. A compound of the structural formula:

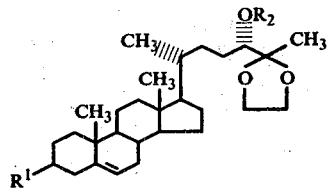

wherein $R^1$ is loweralkanoyloxy; $R^2$ is hydrogen or mesyl.

3. A compound according to claim 2 where $R^1$ is acetoxy.

4. A compound according to claim 1 where $R^2$ is hydrogen.

5. The compound according to claim 1 where $R^1$ is acetoxy and $R^2$ is hydrogen.

UNITED STATES PATENT OFFICE
CERTIFICATE OF CORRECTION

Patent No. 4,145,346              Dated March 20, 1979

Inventor(s)  Howard Jones et al

It is certified that error appears in the above-identified patent and that said Letters Patent are hereby corrected as shown below:

Column 1, Formula II should read as follows:

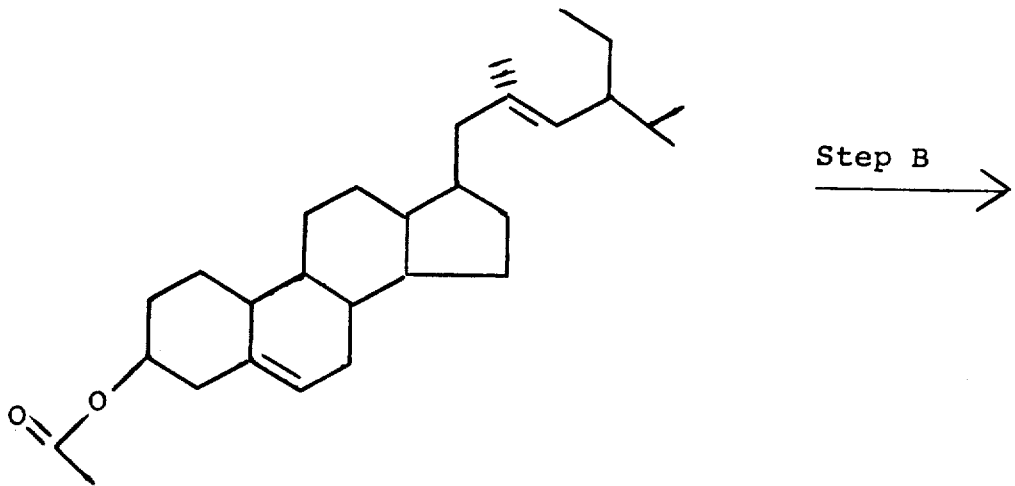

Step B →

Signed and Sealed this

Third Day of July 1979

[SEAL]

Attest:

Attesting Officer

LUTRELLE F. PARKER
Acting Commissioner of Patents and Trademarks